United States Patent
Hearn et al.

(10) Patent No.: US 9,826,779 B2
(45) Date of Patent: Nov. 28, 2017

(54) METHOD OF ASSEMBLING A SIMULATED CIGARETTE

(71) Applicant: Kind Consumer Limited, London (GB)

(72) Inventors: Alex Hearn, London (GB); Ritika Gupta, London (GB); Rene Mauricio Gonzalez Campos, London (GB); Khine Zaw Nyein, Harrow (GB)

(73) Assignee: KIND CONSUMER LIMITED, London (GB)

( * ) Notice: Subject to any disclaimer, the term of this patent is extended or adjusted under 35 U.S.C. 154(b) by 245 days.

(21) Appl. No.: 14/779,919

(22) PCT Filed: Mar. 25, 2014

(86) PCT No.: PCT/GB2014/050941
§ 371 (c)(1),
(2) Date: Sep. 24, 2015

(87) PCT Pub. No.: WO2014/155095
PCT Pub. Date: Oct. 2, 2014

(65) Prior Publication Data
US 2016/0050973 A1   Feb. 25, 2016

(30) Foreign Application Priority Data

Mar. 26, 2013  (GB) .................................. 1305494.5
Mar. 21, 2014  (GB) .................................. 1405079.3

(51) Int. Cl.
*A24F 47/00*   (2006.01)
*A61M 15/00*   (2006.01)
(Continued)

(52) U.S. Cl.
CPC ....... *A24F 47/002* (2013.01); *A61M 15/0091* (2013.01); *A61M 15/06* (2013.01);
(Continued)

(58) Field of Classification Search
CPC . A24F 47/002; A61M 15/06; A61M 15/0091; B65D 83/42; B65D 83/32; B65D 83/36
See application file for complete search history.

(56) References Cited

U.S. PATENT DOCUMENTS 3,721,240 A        3/1973  Tamburri
2011/0290244 A1*  12/2011  Schennum ............ A61M 15/06
                                                           128/200.23
(Continued)

FOREIGN PATENT DOCUMENTS

DE   4030257 A1   4/1992
EP   0824927 A2   2/1998
(Continued)

OTHER PUBLICATIONS

International Search Report and Written Opinion dated Sep. 15, 2014 for Application No. PCT/GB2014/050941.
(Continued)

*Primary Examiner* — Michael J Felton
*Assistant Examiner* — Jerzi H Moreno Hernandez
(74) *Attorney, Agent, or Firm* — Patterson & Sheridan, L.L.P.

(57) ABSTRACT

A method of assembling a tubular simulated cigarette, the method comprising providing an elongate hollow housing having an inhaling end and a refill end; inserting an outlet valve tube, a dip tube and a support from the refill end so that the support supports the proximal end of the dip tube in the housing; inserting a refill valve into the refill end and fixing it in place to form a composition reservoir with the dip tube placing the reservoir in fluid communication with an outlet orifice when the outlet valve tube is open; inserting a valve element into a recess in the side of the housing so that the valve element is positioned to selectively close the outlet valve tube; inserting a breath operated valve actuation (Continued)

mechanism laterally into the recess; and applying a cover to the recess.

12 Claims, 4 Drawing Sheets

(51) Int. Cl.
  *A61M 15/06*  (2006.01)
  *B65D 83/32*  (2006.01)
  *B65D 83/42*  (2006.01)
  *B65D 83/36*  (2006.01)

(52) U.S. Cl.
  CPC ............. *B65D 83/32* (2013.01); *B65D 83/42* (2013.01); *B65D 83/36* (2013.01)

(56) References Cited

U.S. PATENT DOCUMENTS

2011/0290248 A1* 12/2011 Schennum ............ A24F 47/002
                     128/202.21
2012/0090629 A1* 4/2012 Turner ............ A61M 15/06
                     131/273
2012/0138054 A1* 6/2012 Hearn ............ A24F 47/002
                     128/203.12
2012/0318827 A1* 12/2012 Schennum ............ B65D 83/54
                     222/394

FOREIGN PATENT DOCUMENTS

| EP | 2614732 A1 | 7/2013 | |
|---|---|---|---|
| GB | WO 2011117580 A2 * | 9/2011 | ........... A24F 47/002 |
| WO | 2011107737 A1 | 9/2011 | |
| WO | 2011117580 A2 | 9/2011 | |
| WO | 2012129787 A1 | 10/2012 | |

OTHER PUBLICATIONS

United Kingdom Search Report dated Sep. 22, 2014 for Application No. GB1405079.3.

* cited by examiner

METHOD OF ASSEMBLING A SIMULATED CIGARETTE

The present invention relates to a method of assembling a simulated cigarette.

The applicant has proposed a simulated cigarette of the kind having a housing containing a reservoir of inhalable composition having an outlet which is selectively closed by a breath operated outlet valve. This opens when a user sucks on the outlet end to dispense composition from the reservoir.

A simulated cigarette of this type is disclosed in WO2011/107737. This document requires a wick filling a substantial portion of the reservoir in order to ensure that adequate composition is provided to the reservoir outlet when the outlet valve is open whatever the orientation.

A wick is however, less than ideal as the high surface area that it presents to the composition increases the tendency for wick material to leach into the composition.

DE4030257 discloses a tube extending for a short distance from the outlet end of the reservoir. The tube is flexible and has a weight at its inlet end such that it is weighted towards the bottom face of the reservoir, whatever its orientation. The document contains no disclosure of how the simulated cigarette is assembled in practice.

In order to be a successful commercial product, it is important that the simulated cigarette can be assembled simply in a manner which is suitable for mass production.

The present invention is directed to a method of assembling a cigarette which addresses the problems of the prior art and which is suitable for mass production.

According to the present invention there is provided a method of assembling a tubular simulated cigarette, the method comprising:
  a) providing an elongate hollow housing having an inhaling end and a refill end;
  b) inserting from the refill end an outlet valve tube being open at its proximal end and having an outlet orifice at a distal end so that the outlet orifice is adjacent to the inhaling end;
  c) inserting a dip tube from the refill end so that its distal end is in fluid communication with the proximal end of the outlet valve tube;
  d) inserting a support from the refill end to support the proximal end of the dip tube in the housing;
  e) inserting a refill valve into the refill end and fixing it in place, such that the housing in this region of the simulated cigarette forms a composition reservoir with the dip tube placing the reservoir in fluid communication with the outlet orifice when the outlet valve tube is open, the refill valve allowing selective communication with the reservoir;
  f) inserting a valve element into a recess in the side of the housing so that the valve element is positioned to selectively close the outlet valve tube;
  g) inserting a breath operated valve actuation mechanism laterally into the recess; and
  h) applying a cover to the recess.

The invention inserts a number of components into the refill end of the cigarette and a number of other components through a recess in the side of the housing. This provides a simple assembly in that components can be readily guided into place without interfering with one another. Further, the insertion of the support to support the proximal end of the dip tube provides a simple way of retaining the dip tube in the desired position. Thus, the cigarettes can easily be assembled with all of the components reliably located.

It is possible that one or more of the outlet valve tube, dip tube, support and refill valve are integral, or are assembled as a sub-assembly before being inserted into the housing. For example, the outlet valve tube and dip tube may be integrally formed, or the support and refill valve may be inserted as a unitary component. However, preferably, steps b) to e) are separate and sequential.

Steps f) to h) may be separate and sequential. However, preferably the valve element and breath operated valve actuation mechanism are integral and are inserted in a single step.

Steps b) to e) which are the steps requiring the insertion of components into the refill end may be carried out before or after steps f) to h) which are the steps concerned with the lateral opening. However, preferably, step f) occurs after step b) such that the outlet valve tube is put in place before the valve element is in place. This avoids the valve element obstructing or causing potential damage to the outlet valve tube while it is being inserted.

The outer surface of the housing and cover may themselves provide the external surface of the simulated cigarette. However, preferably, after step h), the method further comprises adhering of a wrap to the assembly, the wrap comprising a paper or paper-like layer and a polymer film to protect the paper or paper-like layer. With such a wrap, the cover may not need to be separately fixed to the housing as this can be held in place by the wrap, although it is preferable that the cover is a least temporarily fixed in place before application of the wrap. Most preferably it is permanently fixed with an adhesive, welding or other physical or chemical bonding. The wrap gives the simulated cigarette a cigarette-like look and feel, as disclosed in WO 2011/117580.

A number of the components inserted at the refill end may be separately fixed in place. Preferably, however, the fixing of the refill valve in place maintains the support, dip tube and outlet valve tube in place. Thus, there is no need to separately fix these components.

The refill valve may be held in place by welding, adhesive or snap fitted into place. Preferably it is sonically welded to the housing to form a gas tight seal.

The outlet valve tube can be provided with an orifice that the valve element selectively enters to effectively operate as a gate valve. However, preferably, the outlet valve tube is a deformable tube and the valve element is arranged to selectively pinch the outlet valve tube. Such a pinch valve provides a simple and reliable way of controlling the flow from the reservoir.

The breath operated valve mechanism may be of any suitable design but preferably comprises a diaphragm above which a depression is formed by the user sucking on the outlet end.

Because the support allows the proximal end of the dip tube to be supported within the reservoir, its location can be fixed for optimum performance. The proximal end of the dip tube may be supported towards the refill end of the housing to maximise the amount of composition dispended in a "tip-down" orientation which is the most normal inhaling position. However, preferably, the proximal end of the dip tube is retained such that the main axis of the simulated cigarette passes through the proximal end and so that the dip tube inlet is positioned in the axial sense in the central 50% of the volume of the reservoir. This positions the tube bore inlet towards the centre of the reservoir such that, whatever the orientation of the cigarette, approximately 50% of the liquid can be dispensed. Each time the reservoir is refilled, this allows approximately the same amount of composition to be dispensed regardless of the orientation of the cigarette. This provides a consistent dosage for the user.

Preferably, the dip tube is flexible and the inside of the support has a tapering surface at its distal end to guide the proximal end of the dip tube to the desired location.

An example of a method of assembling a simulated cigarette in accordance with the present invention will now be described with reference to the accompanying drawings, in which.

Figure 1:
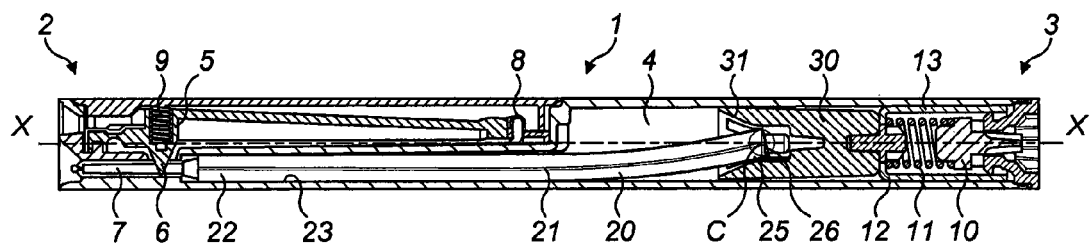
FIG. 1 is an axial cross section through the simulated cigarette.

The basic arrangement of the simulated cigarette is as described in WO2011/107737. Thus, the assembled simulated cigarette has a generally cylindrical shape and is approximately the size of a cigarette. It has a housing 1 with an outlet end 2 and a refill end 3 with a reservoir 4. At the outlet end 2 is a vane 5 with a valve element 6 in the form of a tooth which pinches a resilient tube 7 in order to close the tube. The outlet valve 5 further comprises a vane co-moulded with a diaphragm 8 to open the valve element 6 against the action of a spring 9 when a user sucks on the outlet end 2 as described in WO2011/107737 and in greater detail in UK application 1215278.1.

At the opposite end of the reservoir 4 is the refill valve element 10 which is essentially a check valve which is operable against the action of a second spring 11. This is the subject of GB1305486.1. The second spring 11 and refill valve element 10 are retained in a cage 12 which has a number of openings 13 such that the space within the cage 12 forms part of the reservoir 4.

Figure 7:
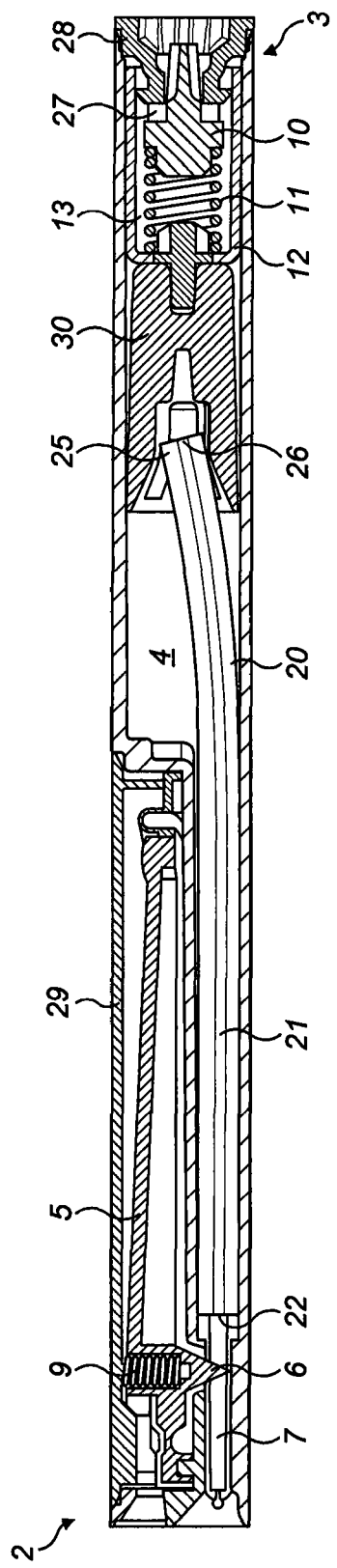
FIG. 7 is a cross sectional view of the second example.

Also within the reservoir 4 is a flexible dip tube 20 with an internal bore 21. The bore 21 has an outlet 22 located adjacent to the end of the resilient tube 7. The dip tube 20 can be placed against (FIGS. 1 to 3) or inside (FIG. 7) the resilient tube 7 so that the composition can only reach the resilient tube 7 via the bore 21. As is apparent from the drawings, it can be either the side wall or the end wall (FIGS. 1 to 3) of the dip tube 20 that seals with the resilient tube 7, but it is preferably both (FIG. 7). If the dip tube 20 is inside the resilient tube 7, the two tubes seal with one another and the resilient tube 7 seals with the housing. It will also be apparent from the drawings that the right hand side of the resilient tube 7 between the valve element 6 and the dip tube 20 is also a part of the reservoir.

At the inlet end 25 of the tube 20, the bore 21 has an inlet 26. The inlet end 25 is supported by a support 30 so that the inlet end 25, and preferably the inlet 26 of the bore 21 is on the main axis X of the housing 1 as shown in FIG. 4.

Figure 4:
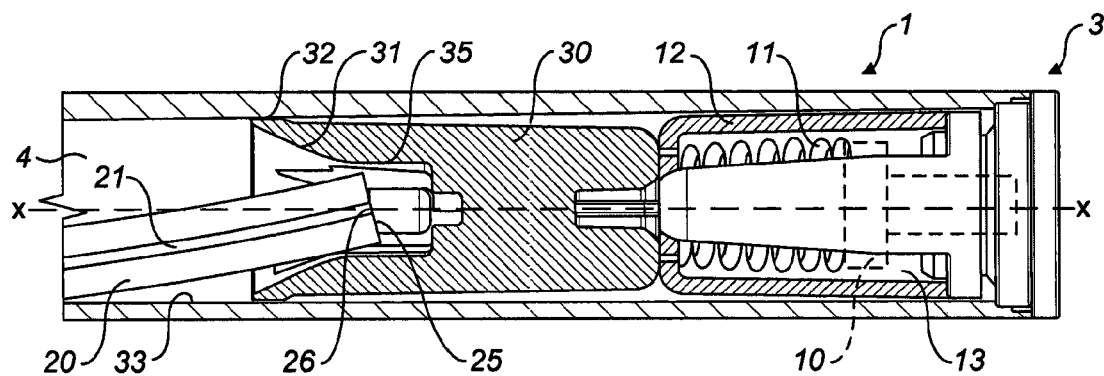
FIG. 4 is an axial cross section showing the right hand portion of FIG. 1 in greater detail.

As best shown in FIG. 4, the support 30 abuts against the valve cage 12 at the end of the support 30 closest to the refill end 3. The support 30 and valve cage 12 may be made as a single component. At the opposite end, the support 30 has a conical face 31 facing towards the outlet end 2. The outer diameter 32 of this end has a similar diameter corresponding to the internal diameter of the reservoir 4 at this point so that the support 30 is an interference fit within the reservoir 4.

Figure 5:
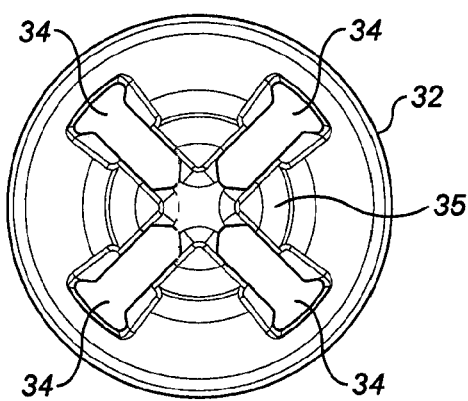
FIG. 5 is an end view of the tube support.

Four openings 34 as shown in FIG. 5 allow the liquid in the reservoir to freely pass the support 30 to gain access to the inlet 26.

Figure 6:
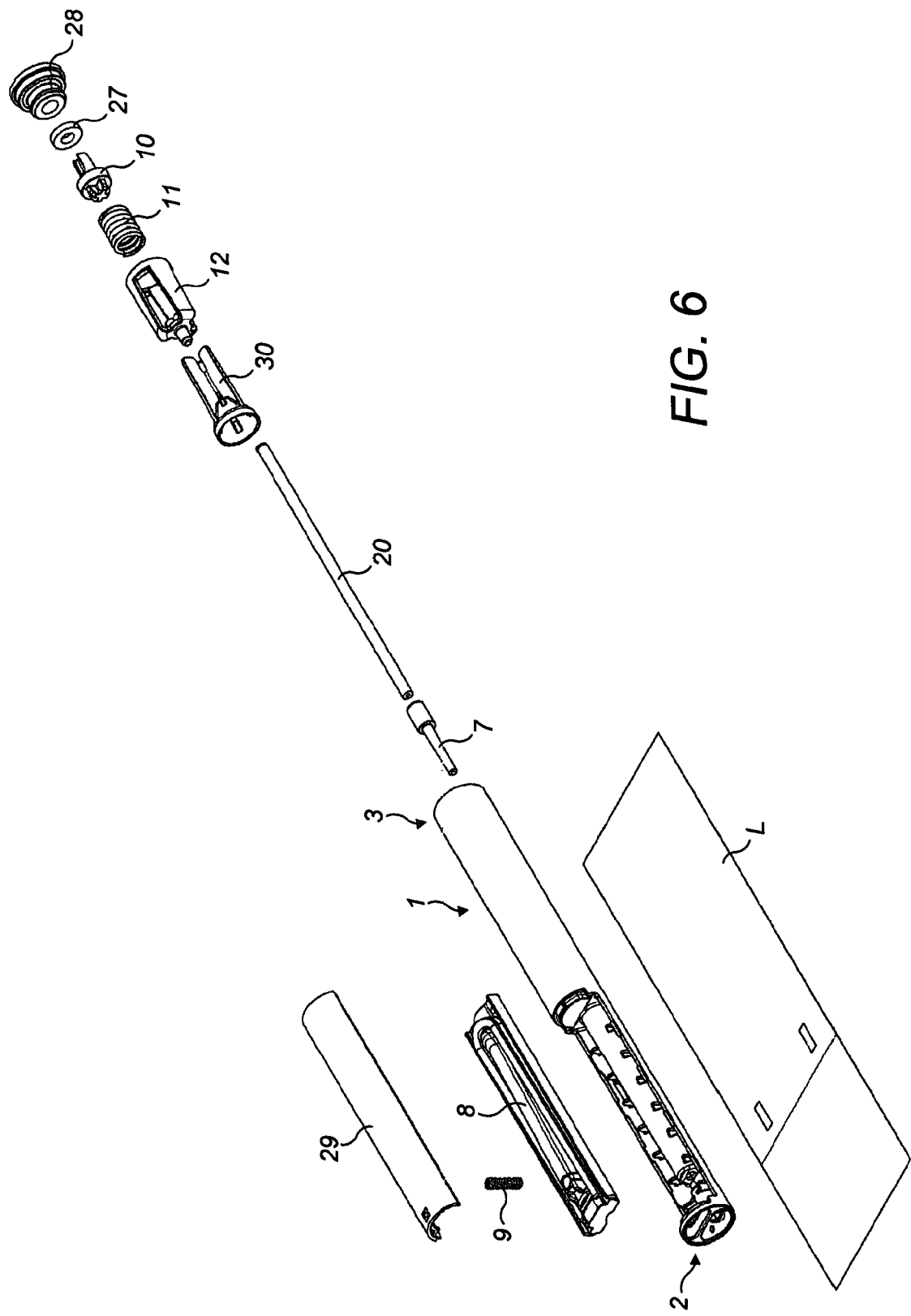
FIG. 6 is an exploded perspective view showing the assembly process of a second example.

The assembly of the simulated cigarette will now be described with reference to FIG. 6 which shows the components in an exploded view.

The simulated cigarette is manufactured in a cleanroom environment preferably BS EN ISO 14644-1: 1999 class 8 clean room or greater. The assembly line can be made up of one or more manual or/and semi-automatic or fully automated assembly stations which can be either standalone or modularly integrated in the same assembly line. In the most preferred design, the cigarette is assembled as set out below.

At the first station, a refill valve sub-assembly is assembled by fitting cage 12, spring 11, refill valve element 10, valve seal washer 27 and end cap 28 together thereby forming a unitary component called a cage valve.

This may be formed at a further station in the production line instead of a pre-formed sub-assembly. The cage valve can be tested for leakage and be further assembled with the support 30 before being integrated in the next assembly station.

At the second assembly station, the housing 1 is placed in a nest and the resilient tube 7 is inserted into the housing 1 followed by the dip tube 20. The said sub-assembled cage valve and the support 30 are then placed into the housing 1 and an ultrasonic cycle is initiated to weld the end cap 28 to the housing 1 thereby clamping and sealing all of the previously inserted components in place.

At the third station, a valve assembly comprising the vane 5, the co-moulded diaphragm 8 and the valve element 6 is loaded onto the housing 1 from the side and ultrasonically welded in place. The spring 9 is then loaded into the recess of the vane 5, and the cap 29 is put in place over the said valve assembly to hold the spring 9 in place and to seal the cylindrical housing. The cap 29 is then ultrasonically welded onto the housing 1.

Quality control may be appropriate at each individual steps and at a final assembly.

The device may be wrapped and can be moved to a further sub-assembly assembly station where a label L is applied onto the device.

It will be appreciated from the drawings and from the above explanation that the shape of the reservoir 4 is complex.

The right hand portion has a generally cylindrical configuration occupying the majority of the diameter of the device while the left hand portion of the reservoir may just be the internal bore 21 of the tube, or there may be a portion of the reservoir on either side of this tube. Further, in the right hand portion, the volume of the reservoir is reduced by the inlet end portion of the tube 20, seal washer 27, the support 30, the valve cage 12, the second spring 11 and the portion of the refill valve element 10 which is within the reservoir. Thus, while the volume of the reservoir 4 can be determined by measuring these components, it may be simpler to determine this experimentally.

The operation of the device will now be described with reference to FIGS. 1 to 3.

When a user sucks on the outlet end 2, the vane 5 lifts. Provided that the inlet 26 of the bore 21 is below the level L of the liquid in the reservoir, the liquid will travel along the bore 21 and will be atomised downstream of the outlet valve element 6 to create a plume for inhalation. FIGS. 1 to 3 show the centroid C of a body of liquid filling the reservoir 4. The inlet 26 of the bore 21 is in the vicinity of the centroid. In this specific example shown in FIG. 1, it is displaced by 1.3 mm from the centroid C towards the refill end 3. In the horizontal orientation shown in FIG. 1, all of the liquid above the level L which represents approximately 50% of the total liquid in the reservoir can be inhaled from the cigarette. When the cigarette is in the tip-down configuration shown in FIG. 2, as the inlet 26 is displaced from the centroid C as described above, slightly more liquid is available than it is in FIG. 1. Conversely, in the tip-up configuration, slightly less liquid is available for inhalation. In a different arrangement, the inlet 26 is at the centroid C, so that there is essentially no variation in dispensing between the three positions. The current preference is for a slight displacement of the inlet 26 towards the refill end from the centroid C as shown as this causes slightly more liquid to be dispensed in the more common tip-down orientation.

Figure 2:
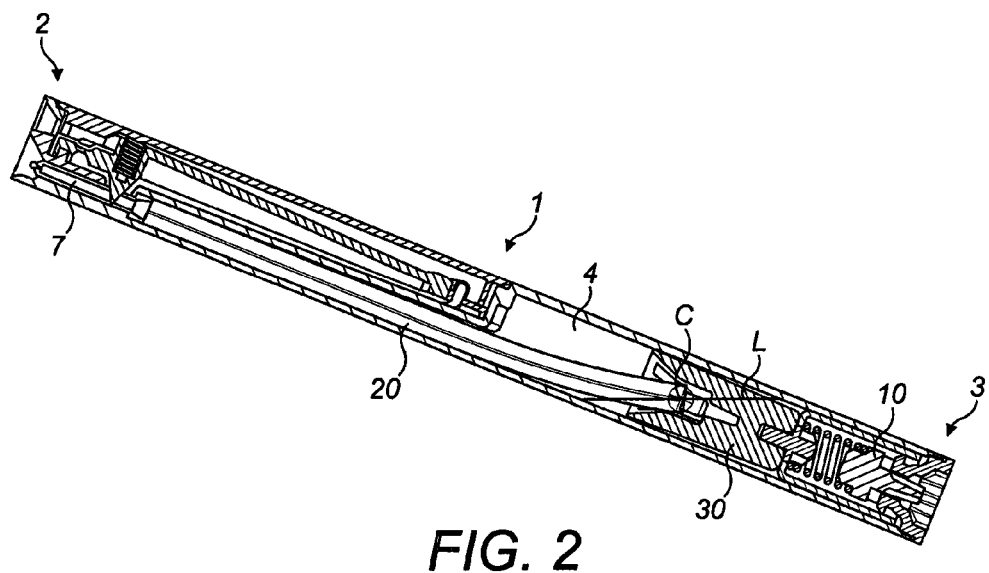
FIG. 2 is a view similar to FIG. 1 in a "tip-down" configuration.
Figure 3:
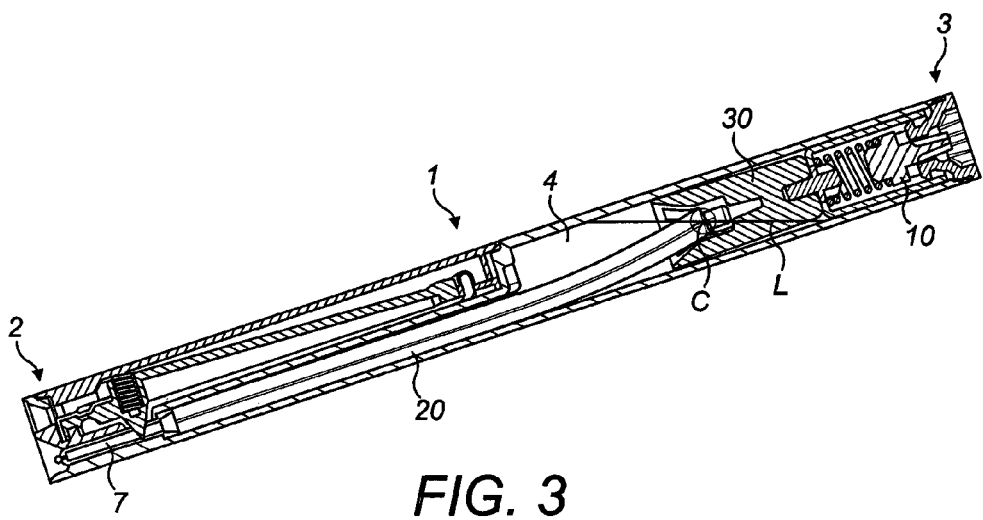
FIG. 3 is a view similar to FIGS. 1 and 2 in a "tip-up" configuration.

Once the liquid level reaches the position L shown in FIGS. 1 to 3, it can be refilled via the refill valve 10 at the user discretion.

The invention claimed is:

1. A method of assembling a tubular simulated cigarette, the method comprising:
   a) providing an elongate hollow housing having an inhaling end and a refill end;
   b) inserting from the refill end an outlet valve tube being open at its proximal end and having an outlet orifice at a distal end so that the outlet orifice is adjacent to the inhaling end;
   c) inserting a dip tube from the refill end so that its distal end is in fluid communication with the proximal end of the outlet valve tube;
   d) inserting a support from the refill end to support the proximal end of the dip tube in the housing;
   e) inserting a refill valve into the refill end and fixing it in place, such that the housing in this region of the simulated cigarette forms a composition reservoir with the dip tube placing the reservoir in fluid communication with the outlet orifice when the outlet valve tube is open, the refill valve allowing selective communication with the reservoir;
   f) inserting a valve element into a recess in the side of the housing so that the valve element is positioned to selectively close the outlet valve tube;
   g) inserting a breath operated valve actuation mechanism laterally into the recess; and
   h) applying a cover to the recess.

2. A method according to claim 1, wherein steps b) to e) are separate and sequential steps.

3. A method according to claim 1, wherein the valve element and breath operated valve actuation mechanism are integral and are inserted in a single step.

4. A method according to claim 1, wherein step f) occurs after step b).

5. A method according to claim 1, further comprising, after step h) adhering of a wrap to the assembly wherein the wrap comprises a paper or paper-like layer and a polymer film to protect the paper or paper-like layer.

6. A method according to claim 1, wherein the support and refill valve are inserted as a unitary component.

7. A method according to claim 1, wherein the fixing of the refill valve in place maintains the support dip tube and outlet valve in place.

8. A method according to claim 1, wherein the refill valve is sonically welded to the housing.

9. A method according to claim 1, wherein the outlet valve tube is a deformable tube and the valve element is arranged to selectively pinch the outlet valve tube.

10. A method according to claim 1, wherein the breath operated valve activation mechanism comprises a diaphragm over which air is arranged to flow through the housing to open the valve element against a biasing member.

11. A method according to claim 1, wherein the proximal end of the dip tube is retained such that the main axis passes through the proximal end so that the dip tube inlet is positioned in the axial sense in the central 50% of the volume of the reservoir.

12. A method according to claim 1, wherein the dip tube is flexible and the inside of the support has a tapering surface at its distal end to guide the proximal end of the dip tube to the desired location.

* * * * *